(12) United States Patent
Anderson

(10) Patent No.: US 7,785,105 B2
(45) Date of Patent: Aug. 31, 2010

(54) APPARATUS FOR MAINTAINING A DRY FIELD DURING DENTAL PROCEDURES

(76) Inventor: Ross William Anderson, 6287 Mercedes La., Plymouth, MI (US) 48170

( * ) Notice: Subject to any disclaimer, the term of this patent is extended or adjusted under 35 U.S.C. 154(b) by 275 days.

(21) Appl. No.: 11/680,848

(22) Filed: Mar. 1, 2007

(65) Prior Publication Data

US 2007/0148619 A1    Jun. 28, 2007

Related U.S. Application Data

(63) Continuation-in-part of application No. 10/994,096, filed on Nov. 19, 2004, now abandoned, which is a continuation-in-part of application No. 10/301,940, filed on Nov. 22, 2002, now abandoned.

(51) Int. Cl.
*A61C 5/00*    (2006.01)
*A61C 17/06*    (2006.01)
*A61B 1/32*    (2006.01)

(52) U.S. Cl. ............................ 433/140; 433/91; 433/93; 433/94; 600/237

(58) Field of Classification Search ................ 433/136, 433/93, 140, 218, 68, 69, 92–94; 600/238; 128/859; D24/135
See application file for complete search history.

(56) References Cited

U.S. PATENT DOCUMENTS

| | | |
|---|---|---|
| 3,049,806 A | 8/1962 | Cofresi |
| 3,916,880 A | 11/1975 | Schroer |
| 4,215,984 A | 8/1980 | Reichley |
| 4,259,067 A | 3/1981 | Nelson |
| 4,260,378 A | 4/1981 | O'Neil |
| 4,354,837 A | 10/1982 | Moore |
| 4,511,329 A | 4/1985 | Diamond |
| 4,592,344 A * | 6/1986 | Scheer ................. 600/242 |
| 4,690,640 A * | 9/1987 | Hinz ..................... 433/6 |
| 4,975,057 A | 12/1990 | Dyfvermark |
| 5,037,298 A * | 8/1991 | Hickham ............... 433/93 |
| 5,152,686 A | 10/1992 | Duggan et al. |
| 5,460,524 A * | 10/1995 | Anderson ............. 433/93 |
| 5,890,899 A | 4/1999 | Sclafani |
| 6,022,214 A | 2/2000 | Hirsch et al. |
| 6,354,833 B1 | 3/2002 | Townsend-Hansen |

OTHER PUBLICATIONS

New Line Dental and Medical Products. DentaPops [online], [retrieved Jul. 22, 2002]. Retrieved from the Internet <URL: http://www.newlinemedical.com/DentaPops.html>.

* cited by examiner

*Primary Examiner*—Cris L Rodriguez
*Assistant Examiner*—Yogesh Patel
(74) *Attorney, Agent, or Firm*—Dorr, Carson & Birney, P.C.

(57) ABSTRACT

An apparatus for maintaining a dry field during dental procedures includes a U-shaped tongue shield for holding the patient's tongue in a retracted position. Cheek distention arms extend laterally outward and forward from the tongue shield to distend the cheek away from the teeth. Lip retractors extend from the cheek distention arms in an arcuate shape above and below the cheek distention arms. Webbing extends between the lip retractors and cheek distention arms to support the soft tissue within the patient's mouth distal to the orbicularis oris muscle.

19 Claims, 6 Drawing Sheets

APPARATUS FOR MAINTAINING A DRY FIELD DURING DENTAL PROCEDURES

RELATED APPLICATIONS

The present application is a continuation-in-part of the Applicant's co-pending U.S. patent application Ser. No. 10/994,096, entitled "Apparatus for Maintaining a Dry Field During Dental Procedures," filed on Nov. 19, 2004, which is a continuation-in-part of U.S. patent application Ser. No. 10/301,940, filed on Nov. 22, 2002.

BACKGROUND OF THE INVENTION

1. Field of the Invention

The present invention relates generally to the field of dental appliances. More specifically, the present invention discloses an apparatus for maintaining a dry field during dental procedures.

2. Statement of the Problem

Throughout the field of dentistry, chairside procedures must be managed to simultaneously achieve a number of objectives. Dentists, orthodontists, prosthodontists, oral surgeons and the like must provide patient comfort while at the same time accomplishing complex therapeutic treatment procedures within the confines of the oral cavity. The clinician must also manage a number of peripheral factors while he or she focuses on achieving worthwhile, long-lasting treatment results. The clinician must strive to minimize such factors as the amount of chair time required to accomplish various treatment goals, the amount of auxiliary staff assistance required as well as overall practice overhead to insure that such professional services remain economically practical for all involved. All of these factors drive dental professionals to embrace improved chairside systems, armamentarium, techniques and procedures that save time, improve results and reduce costs. One aspect of such dental practice economics addressed by the present invention involves those procedures where the polymerization or curing of dental acrylic and various types of dental adhesives must be accomplished. Such procedures typically demand that a dry field be achieved and maintained from the beginning to the end of such procedures. Establishing a dry field involves the isolation of a tooth or a segment a dental arch where tooth surfaces must be cleaned, desiccated, and kept completely dry for the duration of a procedure. In such cases, maintaining dry conditions within the oral environment is essential for the successful, long-term functioning of such cured resins and polymers.

Since tooth enamel and dentin cannot be dissolved by organic solvents, commonly used dental resins and polymers rely on a mechanical bond rather than a chemical bond for adhering such things as orthodontic braces, dental appliances, veneers and sealants, reconstructive prosthesis and composite restorations. Many common bonding procedures involve the preparative step of etching the prepared tooth surfaces with an orthophosphoric or citric acid solution to create a roughened tooth bonding surface. Similarly, it is a common practice to roughen metallic bonding surfaces of various types of dental hardware through a process of vapor abrasion. Vapor abrasion involves directing compressed air carrying micron-sized particles of ceramic carbide or silicon dioxide. Both etching and vapor abrasion prepare the bonding substrates to create greater surface area and greater "purchase" for improved strength and retention of the subsequently-applied adhesive.

Saliva and saliva-borne oral biotica are the nemesis of sound mechanical bonds in that if present, they introduce a release agent of sorts, disrupting the micro inter-articulation of the adhesive with the prepared substrates to be joined. Likewise, for other types of dental polymers such as dental acrylic, moisture serves as an inhibiter of full molecular cross-linking and interferes with the attainment of a complete, amorphous chemical cure throughout the acrylic mass. In such cases where less than complete polymerization is achieved, toxic, unpolymerized monomer may leach into the oral environment. Further, unless a full cure is achieved, such materials do not achieve full strength or full hardness. As can be appreciated, achieving and maintaining a dry field is a critical, yet routine and sequential step required by many types of dental procedures.

As an example of a typical chairside procedure requiring a dry field, U.S. Pat. No. 6,354,833 (Townsend-Hansen) describes the need to maintain dry field conditions while bonding orthodontic brackets to a patient's teeth. The composite resins used for bonding brackets to the exposed tooth surface typically require a completely dry field of operation from start to finish. The enamel is etched at the bond site leaving a roughened surface suitable for resin infiltration. A primer is placed on the etched enamel surface, and the bonding resin is placed on the bracket. The bracket is then positioned on the tooth and allowed to cure chemically or is cured by light irradiation from a dental curing device. In orthodontics, it is well known that saliva contamination of a prepared bonding site will reduce the ultimate strength attained by the cured bonding material and it will significantly increase the likelihood of problematic bracket bond failures during orthodontic treatment.

Saliva is produced in and secreted from the salivary glands. The basic secretory units of salivary glands are clusters of cells called an acini. These cells secrete a fluid that contains water, electrolytes, mucus and enzymes, all of which flow out of the acinus into collecting ducts. Secretion of saliva is under control of the autonomic nervous system, which controls both the volume and type of saliva secreted. The production of saliva is a naturally-occurring continuous process that cannot be temporarily halted or consciously regulated. One aspect then of the many chairside procedures that require a dry field is that the need to evacuate saliva from the mouth is continuous as it collects and puddles in the lower posterior vestibules and under the tongue.

In the dental operatory, the responsibility for removing saliva from a patient's mouth is typically relegated to auxiliary staff personnel, who must periodically manipulate, reposition and activate saliva suction/removal devices. In practice, the actual evacuation of pooled saliva periodically requires a few seconds at each of multiple positions in the mouth. This typical chairside scenario introduces a number of obstacles and limitations for the attending clinician in his or her efforts to achieve treatment-related goals. First, the attending clinician must periodically pause from his or her in-process procedure while saliva is evacuated. This results in an interruption to the clinician's visual and mental focus. The very presence of a second person at chairside alters the ergonomics of the dental operatory and restricts space and free movement. The auxiliary staff member must move their hands in and around the oral cavity to evacuate saliva, again breaking the clinician's field of view, as well as mental focus. The cost associated with the presence of an auxiliary staff member, as well as the cumulative increase in time required for saliva evacuation all combine to increase the overhead costs for the practice, which increases the ultimate cost of treatment. For all of these reasons, the value of improved dry field-related devices and methods can be appreciated and for all of these reasons, improved devices and methods for the removal of saliva have been sought.

In addition to the challenges of saliva control, another fundamental challenge faced by clinicians involves the increased difficulty of performing procedures in the posterior region of the oral cavity. The central problem associated with delivering dental treatment in this region of the mouth is the general restriction of space as well as reduced physical and visual access. The posterior regions of the mouth are inherently darker and less accessible and it is more difficult to direct light where needed. The adjacent bony structures of the anterior aspect of the ramus, and the soft tissue and musculature of the cheeks restrict the clinician's access and prevent a direct or perpendicular line of sight. The confined vestibular space between the buccal surfaces of the posterior teeth and the adjacent soft tissues of the cheeks limits the number and size of dental instruments that can occupy the space, and makes the transportation of dental materials and dental armamentarium in and out of the mouth more difficult.

Yet another challenge routinely faced by the clinician is the interference and unpredictability posed by a free and unruly tongue. Patients typically have little positional awareness of their tongue during treatment, and wide and unpredictable tongue movements can suddenly interfere with the clinician's efforts and focus, and a wandering tongue can potentially contaminate dry field conditions.

Prior Art. The prior art in the field of dentistry and orthodontics includes a wide variety of tongue retractors and devices for extracting saliva, including the following:

| Inventor | Patent No. | Issue Date |
| --- | --- | --- |
| Confresi | 3,049,806 | Aug. 21, 1962 |
| Schroer | 3,916,880 | Nov. 4, 1975 |
| Reichley | 4,215,984 | Aug. 5, 1980 |
| Nelson | 4,259,067 | Mar. 31, 1981 |
| O'Neil | 4,260,378 | Apr. 7, 1981 |
| Moore | 4,354,837 | Oct. 19, 1982 |
| Diamond | 4,511,329 | Apr. 16, 1985 |
| Dyfvermark | 4,975,057 | Dec. 4, 1990 |
| Hickham | 5,037,298 | Aug. 6, 1991 |
| Duggan et al. | 5,152,686 | Oct. 6, 1992 |
| Anderson | 5,460,524 | Oct. 24, 1995 |

"DentaPops", New Line Medical - Dental and Medical Products, http://www.newlinemedical.com/DentaPops.html Anderson discloses a device and method for saliva suction in dental procedures that includes a tongue retractor and bite handle. The embodiment shown in FIG. 12 of the Anderson patent includes a retraction wing or cheek retractor. This device engages the tubing in a manner that directs the suction tubing outward and in contact with the cheeks, thus holding the cheeks away from the teeth.

Confresi discloses a device for suctioning saliva from the oral cavity including a tubular member having inlet orifices on both sides of the teeth and an adjustable brace serving as a tongue depressor.

Reichley discloses a dental suction device having a U-shaped base designed to be positioned on the patient's lower teeth.

Nelson discloses a dental device for isolating a region of the mouth, and includes a frame to retain the device and a shield member to retract the tongue from the lower teeth.

O'Neil discloses a self-stabilizing intra-oral saliva evacuator.

Diamond discloses a moisture-controlling lingual dental mirror.

Dyfvermark discloses a bite block appliance with an aperture serving as an evacuation nozzle for saliva suction.

Hickham discloses an apparatus for ejecting saliva that includes a pair of saliva ejectors connected to a tongue retractor, a cheek retractor connected to a tongue retractor, and a cheek retractor connected to a tongue retainer that is secured to the tongue retractor.

Duggan et al. disclose an appliance for suctioning debris from the oral cavity that includes a tongue stabilizer and a removable suction tube secured to a bite block.

Schroer discloses a device for holding upon the mouth during dental treatment. The device includes lip retractors interconnected by a U-shaped stirrup.

Moore discloses a dental appliance having a collar with a blade-like protrusion and a locking finger for engaging a slotted groove on the cap of a saliva ejector.

The "DentaPops" internet web site discloses a disposable device resembling a candy sucker having a hollow stem for evacuating saliva.

Solution to the Problem. The present invention brings forth a multi-function device that is designed to control, and continuously remove saliva from the mouth without the need for manipulation. It is intended to be used in conjunction with conventional chairside saliva evacuation systems, and is intended to act continuously, thus greatly reducing or eliminating the need for monitoring and manipulation of saliva evacuation equipment. In particular, the cheek distention arms, webbing and lower paddles of the device serve to support the soft tissue inside the cheeks to open the patient's vestibules. The device also includes stanchions and lip retractors with vertical guides aligned to guide insertion of a suction tubes into the vestibules. In addition, the tongue shield control the tongue and create space in, and access to the posterior regions of the mouth.

SUMMARY OF THE INVENTION

This invention provides an apparatus for maintaining a dry field during dental procedures that includes a U-shaped tongue shield for holding the patient's tongue in a retracted position. Cheek distention arms extend laterally outward and forward from the tongue shield to distend the cheek away from the teeth. Lip retractors extend from the cheek distention arms in an arcuate shape above and below the cheek distention arms. Webbing extends between the lip retractors and cheek distention arms to support the soft tissue within the patient's mouth distal to the orbicularis oris muscle.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figure 2:
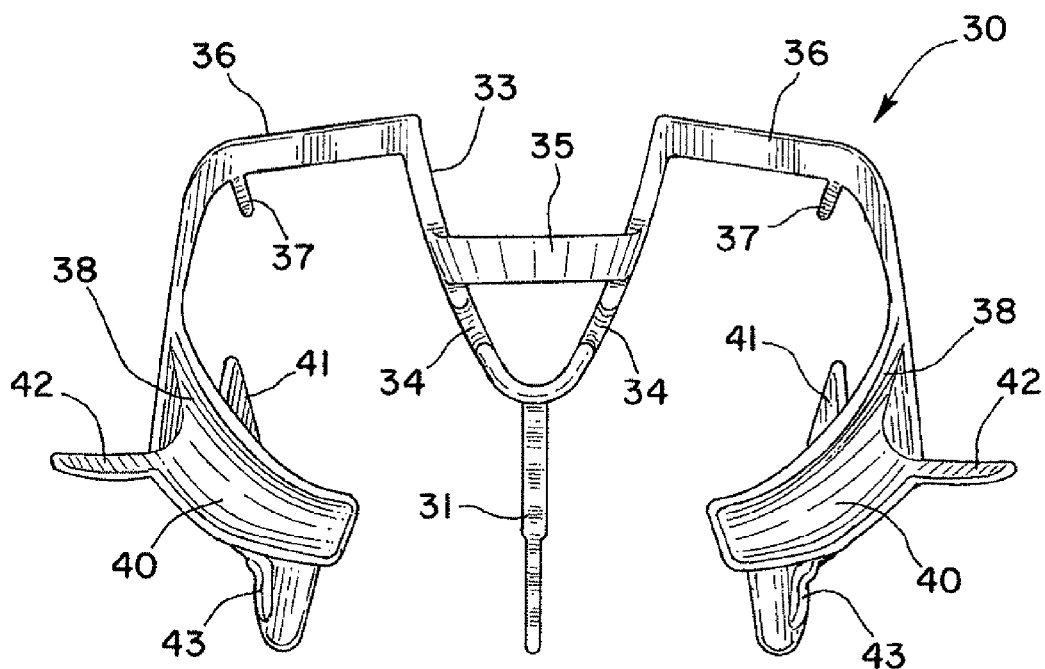
FIG. 2 is a top view of the present device 30.
Figure 3:
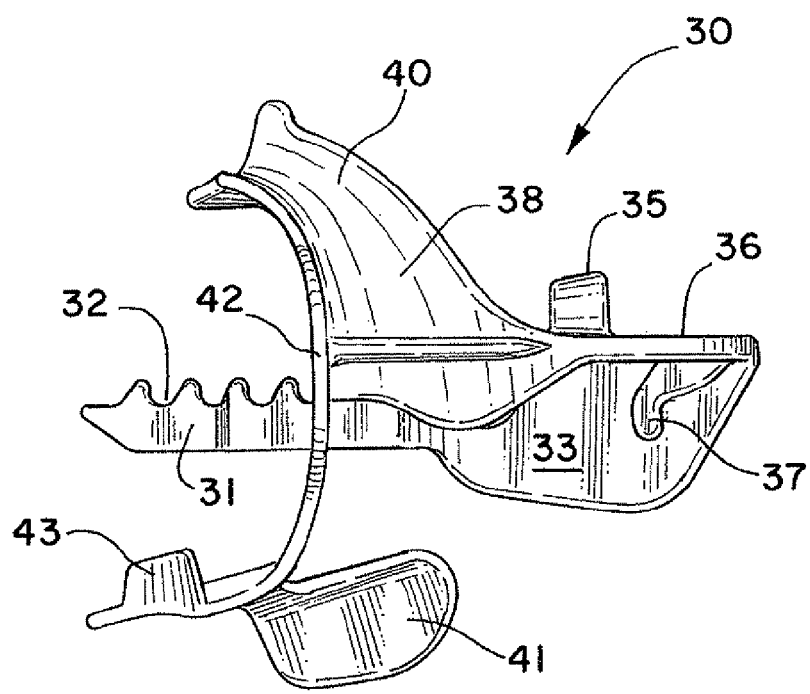
FIG. 3 is a right side elevational view of the present device 30. The left side elevational view is a mirror image of FIG. 3.
Figure 7:
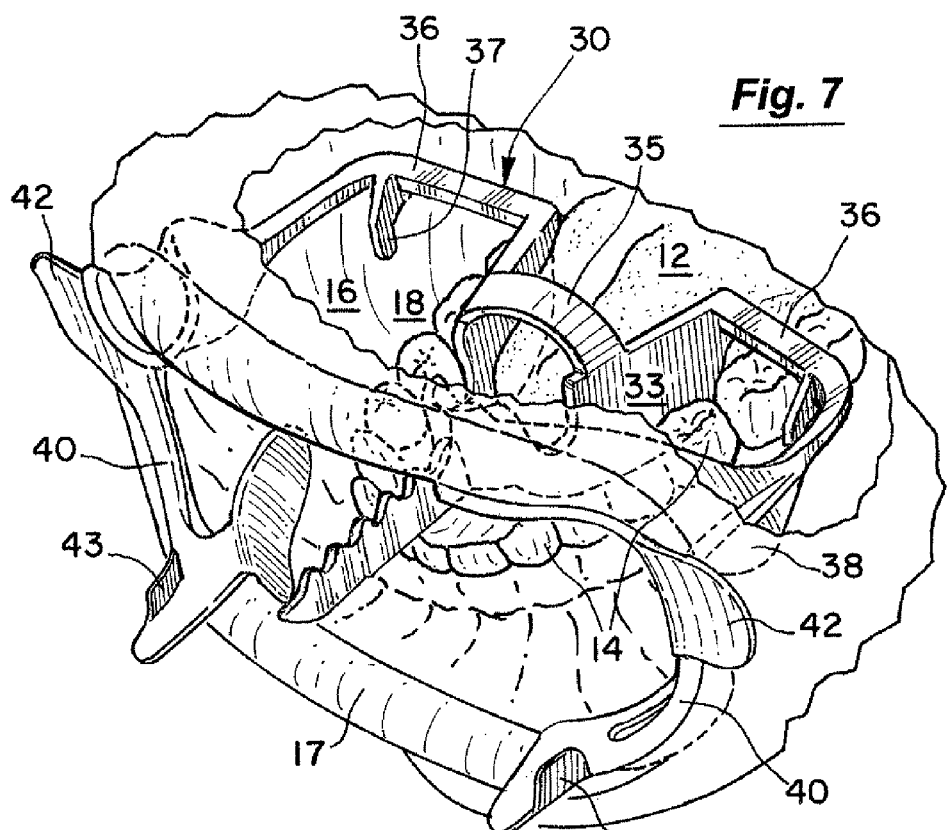
FIG. 7 is a perspective view of the device 30 in place over a patient's lower teeth.

The present invention is a one-piece, preferably injection-molded plastic appliance 30 that is meant to be positioned in the mouth of a patient undergoing a procedure that requires the maintenance of a dry field, or involves procedures in the posterior area for the mouth. As shown in the top perspective view of the device 30 depicted in FIG. 1 the central portion of the appliance 30 is a substantially U-shaped tongue shield 33 with opposing sides that can be placed lingually with respect to a patient's lower teeth to hold a patient's tongue in a retracted position, as shown in FIG. 7. FIG. 2 is top view and FIG. 3 is a right side elevational view of the appliance 30.

An optional bite handle 31 extends forward from the front of the appliance 30. On the top surface of the bite handle 31 are positioning notches 32 of a generally saw-tooth configuration. The saw-tooth configuration consists of a series of identical notches 32, each having a mesial side and distal side and a notch floor. The sides are at predetermined angles relative to the long axis of the bite handle 31 and as such, are optimized to function for optimal mesio-distal stabilizing of the device in the mouth through engagement with a patient's upper and lower central incisor teeth.

In use, the bite handle 31 is gripped by the clinician or staff member by thumb and forefinger pressure and positioned within the patient's mouth in the most rearward position that a patient can comfortably tolerate. Due to the careful sizing of the appliance 30 in terms of its overall width in the preferred embodiment of the present invention, the appliance 30 can be rotated left/right about a vertical axis past the patient's lips and then moved distally into position posterior to the patient's lower teeth, as shown in FIG. 7. As the device 30 is gently pushed distally, a generally U-shaped tongue shield 33 corrals the tongue 12 and desirably restrains the tongue 12 to a rearward position as shown in FIG. 7. The patient is then instructed to bite down on the bite handle 31 and to thereafter maintain gentle closing pressure on the bite handle 31. In doing so, the patient's upper central teeth will naturally fall into registration with one or another of the positioning notches 32, depending on the patient's age and size. As the device 30 is positioned in this manner, the entire device 30 will inherently be centered laterally, and mechanically held in a most posterior position in the patient's mouth. Through positioning and holding the tongue 12 in such a retracted position, it is least likely to pose problems and introduce interruptions during a procedure, and it is least likely to inadvertently contaminate dry field conditions.

Figure 6:
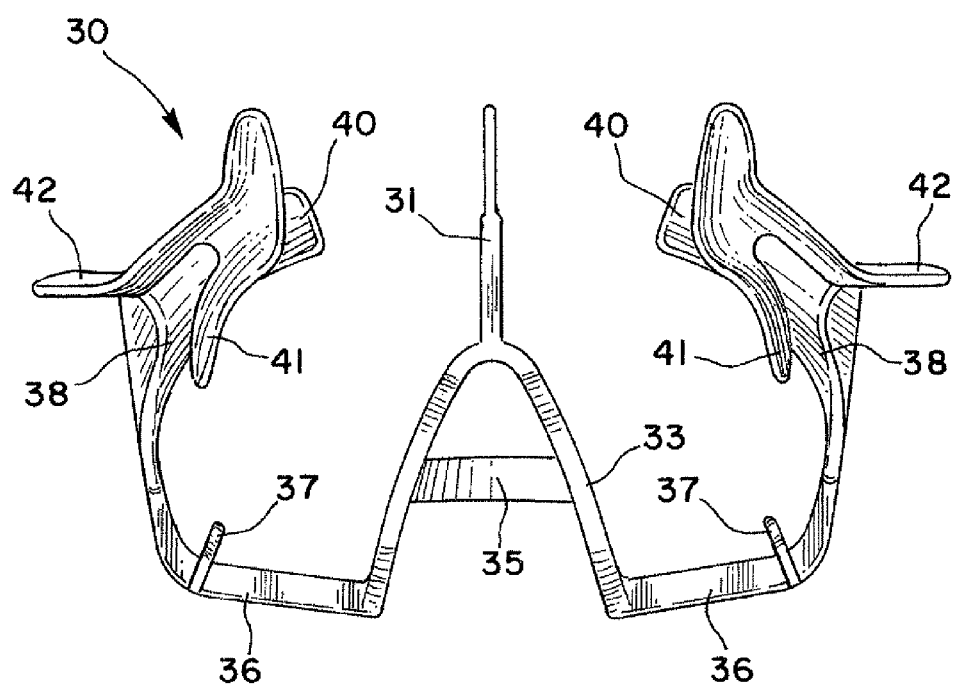
FIG. 6 is a bottom view of the present device 30.

As can be seen in the top view provided in FIG. 2, the bite handle 31 exhibits multiple lateral thicknesses. FIG. 6 is a corresponding bottom view of the appliance 30. As shown, the reduced thickness of the handle 31 at its forward-most end provides a thinner section compared to a thicker distal cross-section. The thinner section provides an ideal ergonomic grip for the thumb and forefinger, while at the same time providing a slightly reduced obstruction for the clinician's labially-directed field of view. The thicker, more distal sections provide structural integrity and stiffness, and as such do not restrict the clinician's line of sight due to parallax. The transition point from a thinner section to a thicker section provides a mechanical stop of sorts for the thumb and forefinger thus aiding the doctor or staff in urging the device 30 as far distally as can be comfortably tolerated by a patient.

It should also be noted that the bite handle 31 can be easily trimmed from the appliance 30, if desired. For example, conventional indirect bonding procedures for brackets used in orthodontics employ a transfer tray that could be obstructed by the bite handle 31.

The positioning notches 32 as shown in the drawings are located on the upper surface of the bite handle 31. As can be appreciated, the positioning notches 32 can function in an identical manner, and equally as effectively if located on the lower surface of the bite handle 31. When located on the lower surface, the top surface of the bite handle 31 can remain smooth and straight. Alternatively, positioning notches 32 could be provided on both the upper and lower surfaces of the bite handle 31.

Figure 1:
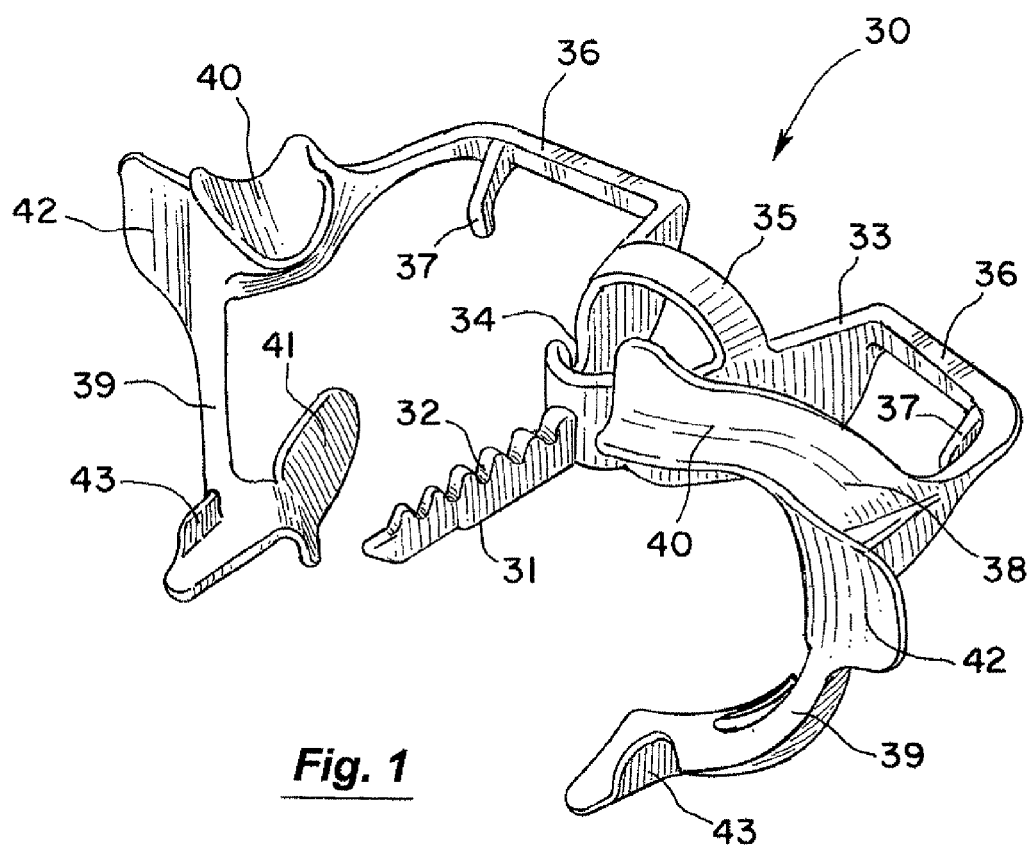
FIG. 1 is a top perspective view of the present device 30.

As shown in FIG. 1, a cross bar 35 extends across the upper portion of the tongue shield 33 above the tongue. This cross bar 35 serves several functions. First, as can be appreciated, the cross bar 35 spans the top of the tongue 12 when the device 30 is positioned in the mouth. In doing so, it functions to further restrain the tongue 12 from significant upward movement. As the cross bar 35 holds the tongue 12 down in this manner, it tends to gently compress the tongue 12 as it passes over it thus forming a shallow trough of sorts in the tongue 12. Such a trough in the tongue 12 serves as a transverse-extending aqueduct of sorts where saliva can collect. Saliva can then flow laterally to points in between the tongue shield 33 and the left and right sides of the tongue 12. As will be described below, the appliance 30 incorporates means for the evacuation of saliva collected from the trough formed by the cross bar 35. The cross bar 35 also acts as a structural member preventing the tongue shield 33 from flexing laterally in use and generally absorbs such stresses, thereby removing some flexural loads on the more forward portions of the tongue shield 33. This allows the tongue shield 33 to be formed thinner in cross-section.

As can be seen in FIGS. 1 and 2, the device 30 has left and right cheek distention arms 36 that extend laterally outward and forward from opposing rear portions of the tongue shield 33 to distend a patient's cheeks away from the molars and vestibules. In the preferred embodiment of the present invention, the arms 36 are substantially L-shaped, as depicted in FIG. 2. The cheek distention arms 36 are generally adjacent to the cross bar 35. The cross bar 35 serves to stabilize the laterally-extending arms 36, again sheltering the tongue shield 33 from bending loads and torsional forces transmitted from the left and right cheek distention arms 36, which permits the tongue shield 33 to be designed with a thinner cross-section.

As the reader can appreciate, the improved features of the present inventive device address one clinical problem described above which involves restraining the tongue 12 in a most rearward position and further acts to prevent upward movement of the tongue 12. Another problem faced by clinicians as described above is the general increased difficulty associated with treatment procedures in the posterior sections of the mouth due to constricted space, limited access and an obstructed line of sight. The present invention generally addresses these problems by providing structure for holding the patient's cheeks 16 well away from the posterior teeth 14 and thus creating a volume of open working space at each side of the mouth, thereby generally improving access to the rear portions of the mouth.

Figure 4:
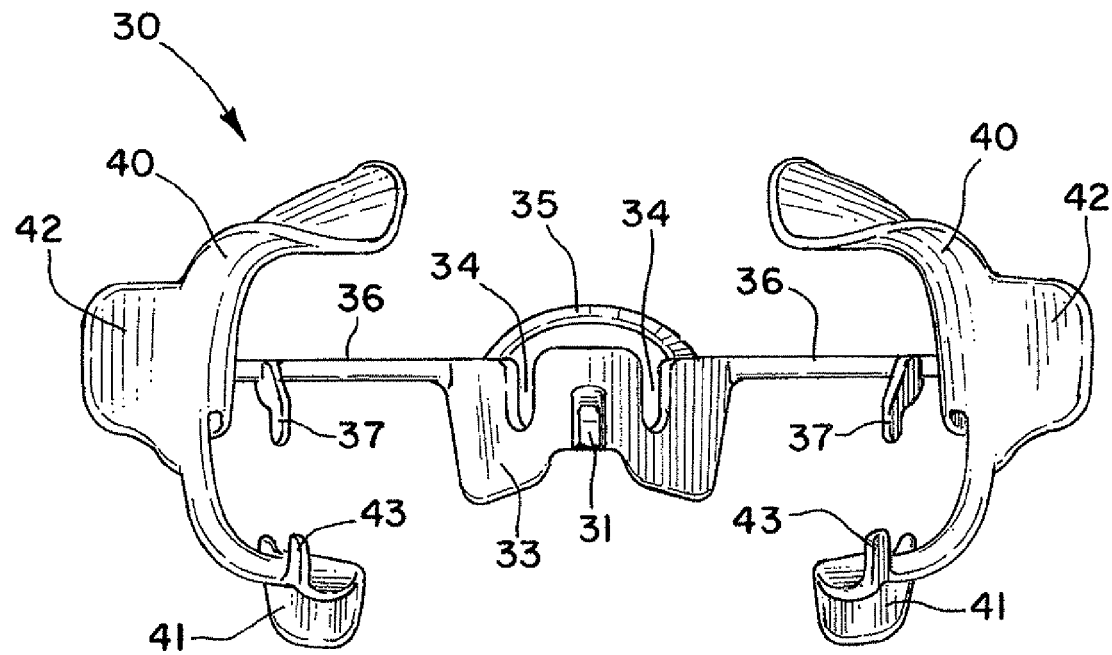
FIG. 4 is a front elevational view of the present device 30.
Figure 5:
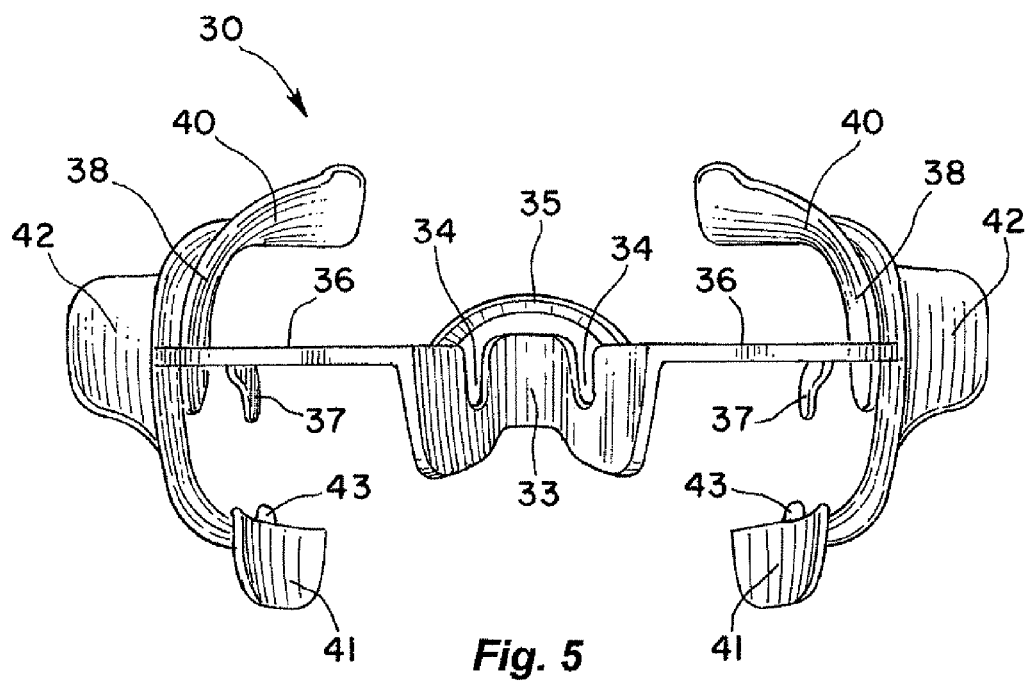
FIG. 5 is a rear elevational view of the present device 30.
Figure 10:
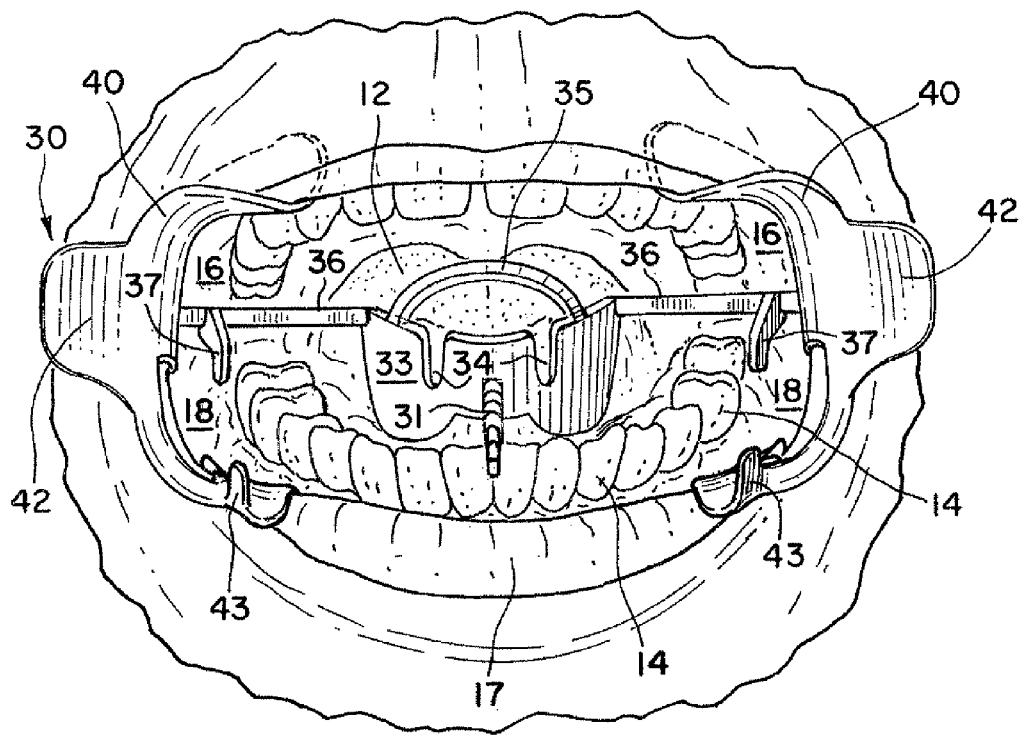
FIG. 10 is a front view of the device 30 in a patient's mouth.
Figure 11:
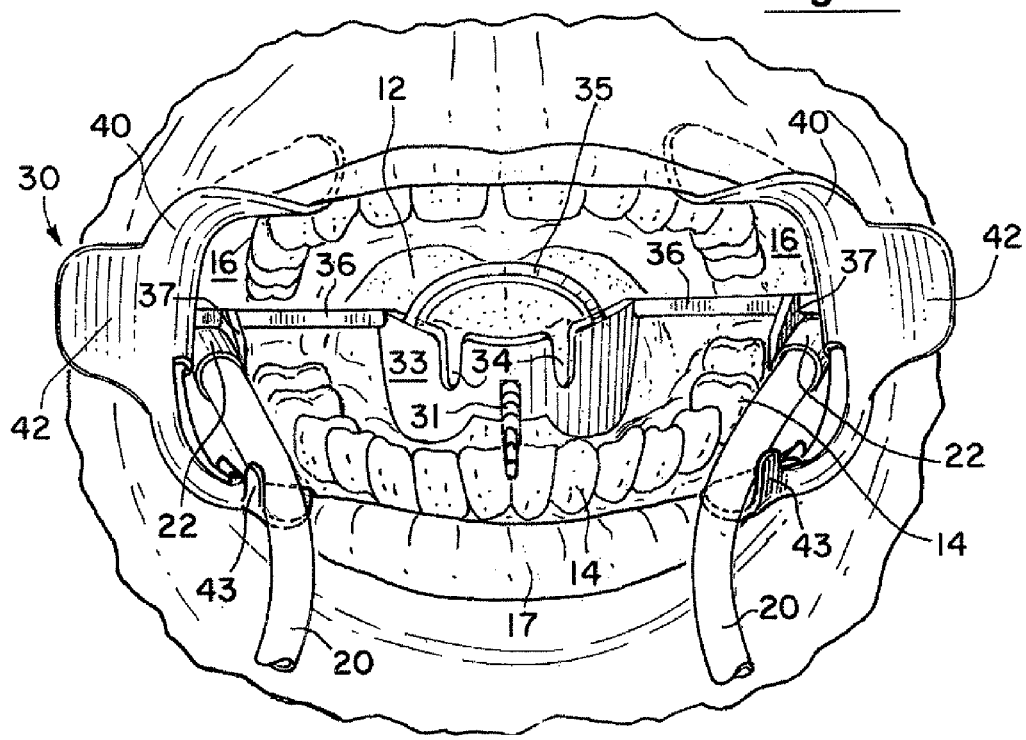
FIG. 11 is a front view corresponding to FIG. 10 with saliva ejectors 20 in place on either side of the device 30.

The present appliance 30 includes two lip retractors 40 that extend forward from anterior portions of the cheek distention arms 36, as shown in the front view of FIG. 4. FIG. 5 depicts a corresponding rear view of the appliance 30. The forward portions of the lip retractors 40 are generally arcuate in shape and extend above and below the medial plane of the cheek distention arms 36 with a contour selected to retract the patient's lips outward and rearward, and thereby maintain the patient's mouth in an open position to maximize the clinician's field of view. FIG. 7 is a perspective view of the device 30 in place in a patient's mouth. FIGS. 10 and 11 are corresponding front views of the appliance 30 in a patient's mouth.

The rearward forces exerted by the lip retractors 40 are countered by forward pressure exerted by the tongue shield 33 on the lingual side of the patient's lower arch. The U-shaped tongue shield 33 also tends to keep the appliance 30 laterally centered within the patient's lower arch. This dynamic balance tends to hold the appliance 30 in place in the proper position in the patient's mouth.

As shown in the side elevation view depicted in FIG. 3, webbing 38 extends between the lip retractors 40 and cheek distention arms 36. In the specific embodiment shown in the drawings, this webbing 38 extends upward from the anterior portions of the cheek distention arms 36 to the upper posterior portions of the lip retractors. In particular, the webbing 38 supports and deflects the soft tissue within the patient's mouth distal to the orbicularis oris muscle This helps to open the vestibules by supporting, pushing or holding out the soft inner tissue of the cheeks.

Optionally, two paddles 41 extend rearward from the lower portions of the lip retractors 40 to further support the soft tissue within the lower portion of the patient's mouth distal to the orbicularis oris muscle. These lower paddles 41 work in combination with the cheek distention arms 36, webbing 38 and lip retractors 40 to support the soft inner tissue of the cheeks and make it somewhat taut.

In the preferred embodiment of the present invention, the overall width of the device 30, including the cheek distention arms 36, lip retractors 40, lower paddles 41 and webbing 38, is maximized so that only through sequential rotating and gentle stretching steps can the device 30 be inserted into a patient's mouth. Importantly, the overall width of the posterior end of the tongue shield 33 is considered and then the lengths of the cheek distention arms 36 are ergonomically maximized so that the rotating, sequential insertion steps require the patient's lips to be stretched to a comfortable maximum. In this sense then, the overall width of the device is designed to be as wide as possible for insertion.

In the broadest sense, all dental procedures can be conceptually divided into two groups, adult procedures, and toddler/infant/adolescent procedures. Adult procedures involve general dental care, prosthetic and reconstructive procedures and others. Procedures directed to the toddler/infant/adolescent group involve pedodontic and orthodontic treatment and other procedures. As can be appreciated, the present device can be formed in multiple sizes, and each size can be thought of as being as wide as possible for the respective patient population in each group. The present invention can be optimized in this manner for maximum ideal width for any patient age/size population and provides the advantage of holding a patient's cheeks outward to a maximum-possible extent permitted by the patient's lip musculature.

In the embodiment of the invention shown in the drawings, two opposing side ears 42 extend laterally outward from the front edges of the lip retractors 40 to facilitate a degree of lateral compression of the device 30. These side ears 42 to allow the dentist to hold and squeeze the device 30 laterally prior to insertion in the patient's mouth. The cross-sectional dimensions of the cheek distention arms 36 posterior to the webbing 38 are selected to allow a safe degree of lateral flexing (or compression) of the appliance 30, which in turn allows the appliance to be inserted more readily into a patient's mouth (i.e., for sizing and comfort). Similarly, the small lobe on the bottom of the side ear 42 of each lip retractor 40 and the accompanying regions of reduced thickness 39 on the lower portions of each lip retractor 40 allow a degree of vertical compression and flexing that can be used to temporarily reduce the cross-sectional area of the appliance 30 during insertion into a patient's mouth.

Figure 8:
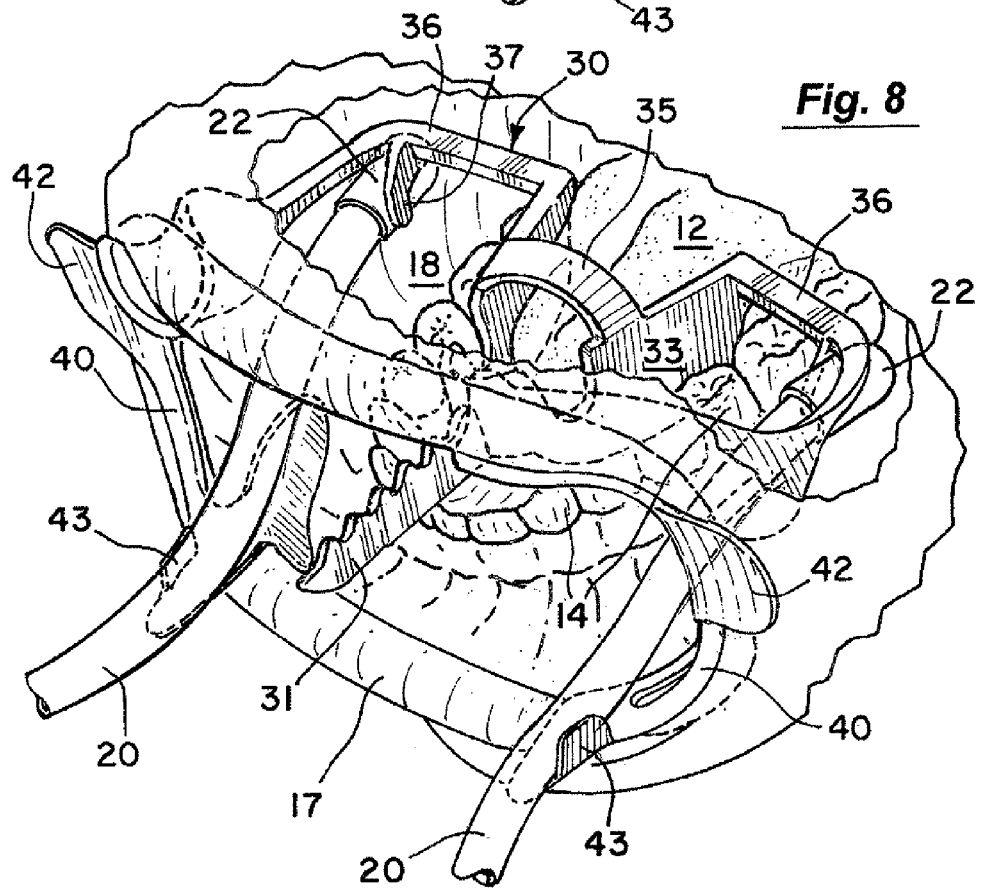
FIG. 8 is a perspective view corresponding to FIG. 7 showing the device 30 in place over a patient's lower teeth with a saliva ejector 20 in place adjacent to one of the stanchions 37.

Optionally, the device 30 can be equipped with stanchions 37 that extend downward near the outer extent of the cheek distention arms 36 to assist in removably positioning the tip 22 of a standard saliva evacuator 20, as illustrated in FIGS. 8 and 11. Known more commonly as saliva ejectors, these are a commodity-type dental supply item available from many dental supply sources. Saliva ejectors 20 are sized to accommodate standard operatory suction tubing, which is in turn connected to a central remote vacuum pump. The operatory suction tubing can employ a Y-shaped fitting so that multiple saliva ejectors can be simultaneously used during a patient's treatment if needed. Standard saliva ejectors exhibit a hollow tube portion and an interconnected hollow head or tip 22. The tubing portion consists of a pliable plastic tube. A compliant, ductile metallic wire is embedded within the walls of the plastic tubing. When the tubing is bent or adapted as needed in use, the embedded wire likewise bends and tends to allow the tubing to take on and retain any gentle shape that a staff member may form in the tubing. For example, the saliva ejector may be shaped similar to a question mark to allow it to simply hang from a patient's lower lip with the head located in the mouth.

The head 22 of the saliva ejector 20 is formed from a somewhat harder plastic than the ductile plastic/metallic wire tubing section. The tubing section and the head 22 are structurally joined to form a single unit. The head 22 exhibits multiple slits that open into the hollow interior. In use, the lower air pressure produced by a central vacuum pump, which is conveyed through the tubing causes air to be drawn into the saliva evacuator head 22 through its multiple slits located circumferentially around its exterior. In use, when the head 22 of the saliva ejector 20 is placed in a pool of saliva, the lower pressure within the interior of the head 22 picks up saliva, which is then drawn out of the mouth and away from the patient through the system of suction tubing.

After the appliance 30 has been inserted into the patient's mouth and the lips have been retracted, a saliva ejector 20 can be positioned by the stanchions 37 on either or both sides of the appliance, as needed. As previously discussed, the stanchions 37 extend downward from the cheek distention arms 36 and can be used to removably hold the head 22 of a saliva ejector 20 against the soft inner tissue of the patient's cheek, as illustrated in FIGS. 8 and 11. Once the saliva ejector 20 has been positioned in the vestibule, the present device 30 provides the benefit of continuous saliva evacuation. Thus, in this embodiment, the stanchions are merely barriers to support a saliva ejector 20 against the interior of the cheek as shown in FIG. 8.

Alternatively, the stanchions could be designed to engage slits in the head 22 of a saliva ejector 20 by frictional fit. Other means can be employed to enable the stanchion 37 to removably engage the head 22 of a saliva ejector 20 in place of, or in addition to frictional contact. For example, the stanchion 37 could be equipped with a connector or fastener (e.g., hook-and-loop material, a clasp mechanism, a hook-and-eye fastener, adhesive, a magnet, a clip, or a snap fastener) for attachment to the saliva ejector 20. The saliva ejector can also be equipped with a complementary connector or fastener, either as an integral part of the saliva ejector or as an attachment.

The saliva ejector 20 is typically placed between the stanchion 37 and the patient's cheek 16 so that the tip 22 of the saliva ejector 20 is located in the patient's vestibule 18 outboard of the stanchion 37. As can be seen in the figures, the stanchions 37 extend downward from the lower surface of both the right and left cheek distention arms 36. In this manner, the clinician or an auxiliary staff member can position one saliva ejector unilaterally or multiple saliva ejectors bilaterally after insertion the present device 30 in the patient's mouth.

Figure 9:
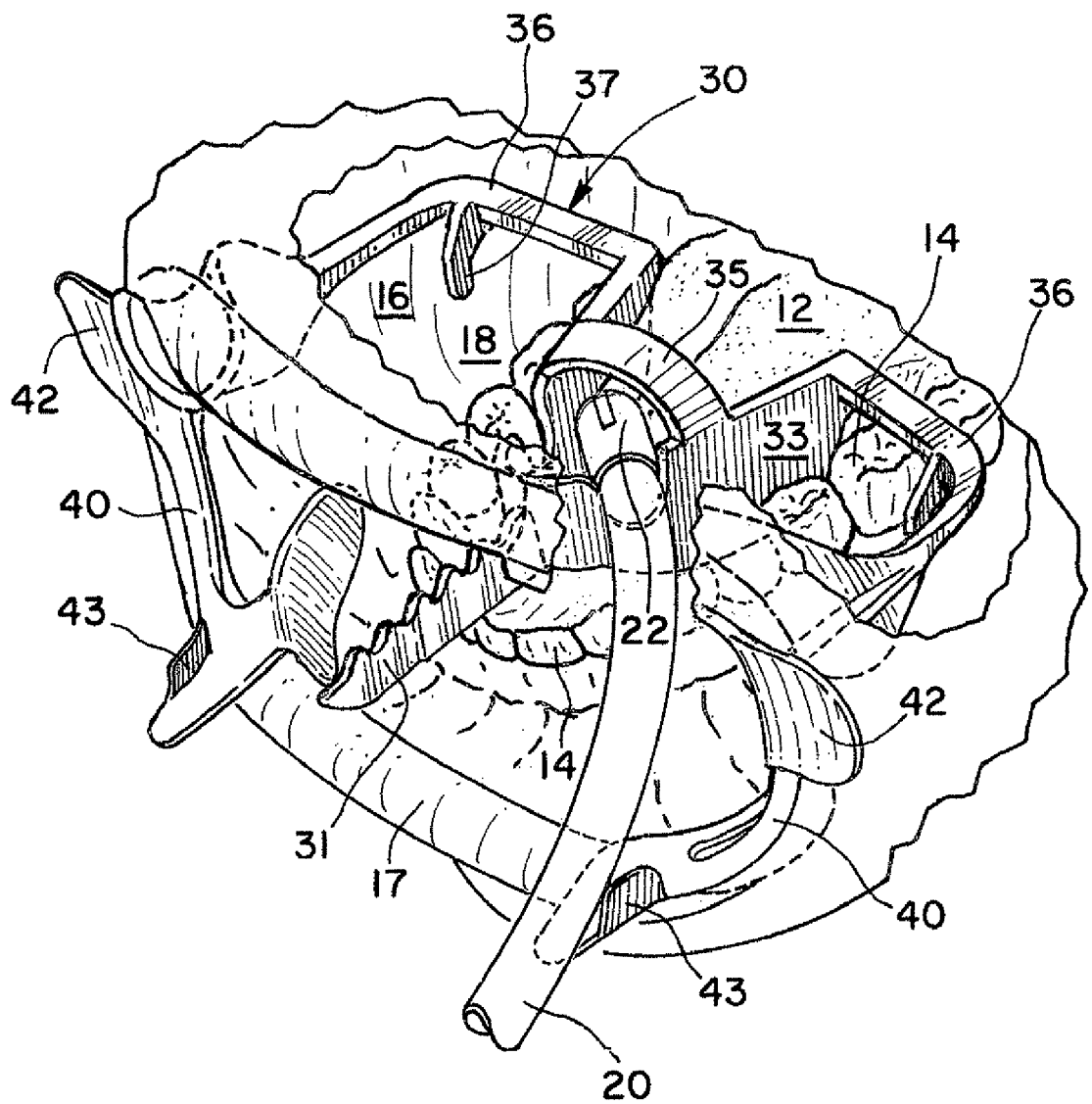
FIG. 9 is a perspective view corresponding to FIG. 7 showing the device 30 in place over a patient's lower teeth with a saliva ejector 20 held in a notch 34 in the tongue shield 33.

Saliva ejectors 20 may be connected to the present device in other useful ways and in other useful positions and combinations. As seen in FIGS. 1 and 9 suction tube notches 34 formed on each side of the tongue shield portion 33 could be employed to accept the placement of a saliva ejector 20. Rather than using the stanchions 37, saliva evacuators 20 engaging the tongue shield 33 rely on a mechanical interfit between a notch 34 of a pre-determined width and the tubing portion of a saliva ejector 20. The left and right suction tube notches 34 formed in the tongue shield 33 are wider than the diameter of typical saliva ejector tubing allowing it to enter the interior area of the tongue shield 33 at an angle slightly more divergent than the natural angle defined as the tubing enters the mouth from a right-most or left-most point of the patient's lips, as shown in FIG. 9. Such sizing of the suction tube notches 34 provides adequate mechanical binding to hold a saliva ejector 20 in place. Saliva gathered in a trough formed by the cross bar 35, as described previously can also be evacuated with saliva ejectors 20 positioned in this manner.

As can be appreciated, a dental professional, if operating on the left side of the mouth may for example place one saliva ejector 20 at the left stanchion 37. That saliva ejector 20 may then be quickly and without difficulty moved to the right side should the clinician then perform the same procedure on the right side. Other types of procedures may require the simultaneous usage of saliva ejectors 20 on both sides as shown in FIGS. 8 and 11. Yet another procedure may require that a saliva ejector 20 be lodged in the notches 34 of the tongue shield 33 as shown in FIG. 9. In this manner, saliva ejectors 20 can be employed in several positions and combinations, and then easily changed as a dental procedure progresses as needed.

Optionally, the lip retractors 40 can also be equipped with guides, notches or openings to facilitate passage of the saliva ejectors 20. These guides further serve to support the saliva ejector 20 in desired locations relative to the appliance 30 and the patient's anatomy. For example, FIGS. 1, 7 and 8 show two vertical guides 43 on the lower portions of the lip retractors 40. These vertical guides 42 are aligned with the stanchions 37 and medial surfaces of the lip retractors 40 to serve are points of contact to guide insertion of a suction tube 20 and then support the suction tube 20 in place.

As can be appreciated, the inwardly-directed pressures of the retracted lips and cheeks and associated musculature on the appliance 30 in use can be significant. The cross-section profile of the cheek distention arms 36, lip retractors 40 and their associated structures are configured to exhibit an adequate cross-section to structurally accommodate such loads, and are further intended to flex and comply somewhat under such loads without significant bending. For safety, the device is formed from materials know to fail in a non-catastrophic mode. Polyethylene, polypropylene, polysulphone and other moderately soft and moderately ductile plastics are known to be biocompatible, pliable, and exhibit mechanical properties that will not yield or fail catastrophically. A brittle plastic could otherwise snap under heavy contraction of the facial musculature, producing sharp failed ends that could lacerate the soft tissues of the mouth.

The present dental appliance 30 can be molded from plastic as a single piece, for example. Alternatively, the appliance could be made of composite materials, such as a glass-reinforced polymer. It may be simpler to fabricate the appliance in several pieces and then bond or otherwise assemble the pieces together to form the final dental appliance. In particular, the lip retractors 40 have a rather complex shape that may be better suited to fabrication in separate molds. Considering the group of commercially-available bioengineering plastics from which devices of the present invention could be formed, some have non-catastrophic failure characteristics and can tolerate heat sterilization without degradation, but are expensive. Other plastics are inexpensive but cannot survive the temperatures associated with sterilization. Given this range of material properties, the present invention is envisioned as being available in inexpensive disposable versions that are discarded after a single use as well as sterilizable versions that could be used repeatedly. In addition, at all points on the device, all edges and corners enjoy extensive radiusing and rounding allowing the present device to sit comfortably within a patient's mouth, preferably without pressure points or any pinching of the patient's tongue, lips or cheeks.

The above disclosure sets forth a number of embodiments of the present invention. Other arrangements or embodiments, not precisely set forth, could be practiced under the teachings of the present invention and as set forth in the following claims.

I claim:

1. An apparatus for maintaining a dry field in a portion of a patient's mouth, said apparatus comprising:
    a substantially U-shaped tongue shield with opposing sides for placement lingually with respect to a patient's lower teeth to hold a patient's tongue in a retracted position;
    cheek distention arms extending laterally outward from opposing rear portions of the tongue shield to distend a patient's cheeks away from the patient's molars in the posterior vestibules with anterior portions extending forward;
    lip retractors extending from the cheek distention arms in an arcuate shape having upper portions above and lower portions below the cheek distention arms;
    webbing extending upward from the anterior portions of the cheek distention arms to the upper portions of the lip retractors to support the soft tissue within the patient's mouth distal to the orbicularis oris muscle; and
    lower paddles extending rearward from the lower portions of the lip retractors to further support the soft tissue within the patient's mouth.

2. The apparatus of claim 1 further comprising a bite handle extending forward from the tongue shield.

3. The apparatus of claim 1 further comprising a cross bar extending across the upper portion of the tongue shield above the tongue.

4. The apparatus of claim 1 further comprising at least one notch in the tongue shield for supporting a saliva ejector in a desired location.

5. The apparatus of claim 1 further comprising a stanchion extending downward from a cheek distention arm for holding a saliva ejector in a desired position.

6. The apparatus of claim 1 further comprising at least one vertical guide on the lip retractors to guide insertion of a suction tube.

7. The apparatus of claim 1 wherein the cheek distention arms are substantially L-shaped and enable a degree of lateral compression of the lip retractors during insertion into a patient's mouth.

8. The apparatus of claim 1 wherein portions of the lip retractors have reduced thickness to enable a degree of vertical compression of the lip retractors during insertion into a patient's mouth.

9. An apparatus for maintaining a dry field in a portion of a patient's mouth, said apparatus comprising:
- a substantially U-shaped tongue shield with opposing sides for placement lingually with respect to a patient's lower teeth to hold a patient's tongue in a retracted position;
- substantially L-shaped cheek distention arms extending laterally outward from opposing rear portions of the tongue shield to distend a patient's cheeks away from the patient's molars and in the posterior vestibules with anterior portions extending forward;
- lip retractors extending from the cheek distention arms in an arcuate shape having upper portions above and lower portions below the cheek distention arms;
- webbing extending upward from the anterior portions of the cheek distention arms to the upper portions of the lip retractors to support the soft tissue within the upper portion of a patient's mouth distal to the orbicularis oris muscle; and
- lower paddles extending distally from lower portions of the lip retractors to support the soft tissue within the lower portion of a patient's mouth distal to the orbicularis oris muscle.

10. The apparatus of claim 9 further comprising a bite handle extending forward from the tongue shield.

11. The apparatus of claim 9 further comprising a cross bar extending across the upper portion of the tongue shield above the tongue.

12. The apparatus of claim 9 further comprising at least one notch in the tongue shield for supporting a saliva ejector in a desired location.

13. The apparatus of claim 9 further comprising a stanchion extending downward from a cheek distention arm for holding a saliva ejector in a desired position.

14. The apparatus of claim 9 further comprising at least one vertical guide on the lip retractors to guide insertion of a suction tube.

15. An apparatus for maintaining a dry field in a portion of a patient's mouth, said apparatus comprising:
- a substantially U-shaped tongue shield with opposing sides for placement lingually with respect to a patient's lower teeth to hold a patient's tongue in a retracted position;
- cheek distention arms extending laterally outward from opposing rear portions of the tongue shield to distend a patient's cheeks away from the patient's molars in the posterior vestibules with anterior portions extending forward;
- lip retractors extending from the cheek distention arms in an arcuate shape having upper portions above and lower portions below the cheek distention arms; and
- webbing extending upward from the anterior portions of the cheek distention arms to the upper portions of the lip retractors to support the soft tissue within a patient's mouth distal to the orbicularis oris muscle;
- at least one stanchion extending downward from a cheek distention arm;
- at least one vertical guide on a lower portion of the lip retractors to guide insertion of a suction tube with the stanchion into a patient's vestibule; and
- lower paddles extending rearward from the lower portions of the lip retractors to further support the soft tissue within the patient's mouth.

16. The apparatus of claim 15 further comprising a bite handle extending forward from the tongue shield.

17. The apparatus of claim 15 further comprising a cross bar extending across the upper portion of the tongue shield above the tongue.

18. The apparatus of claim 15 wherein the cheek distention arms are substantially L-shaped and enable a degree of lateral compression of the lip retractors during insertion into a patient's mouth.

19. The apparatus of claim 15 further comprising at least one notch in the tongue shield for supporting a saliva ejector in a desired location.

* * * * *